United States Patent
Deibert

[19]
[11] Patent Number: 6,063,170
[45] Date of Patent: May 16, 2000

[54] AIR FILTRATION SYSTEM

[75] Inventor: Ronald H. Deibert, Calgary, Canada

[73] Assignee: Air-A-Medic Corporation, Calgary, Canada

[21] Appl. No.: 08/650,862

[22] Filed: May 20, 1996

[51] Int. Cl.[7] .................................................. A61L 2/10
[52] U.S. Cl. .................. 96/224; 95/211; 96/227; 96/288; 261/80; 422/24; 422/121
[58] Field of Search .............................. 96/224, 227, 226, 96/288, 287; 261/80; 95/211; 422/24, 121

[56] References Cited

U.S. PATENT DOCUMENTS

| | | | |
|---|---|---|---|
| 1,817,442 | 8/1931 | Martin, Jr. ................................. | 261/80 |
| 1,818,391 | 8/1931 | Greene ....................................... | 261/80 |
| 2,638,644 | 5/1953 | Rauhut ................................. | 92/224 X |
| 3,203,676 | 8/1965 | Sprouse et al. ...................... | 96/288 X |
| 3,487,620 | 1/1970 | Klein et al. ............................ | 96/227 X |
| 3,756,311 | 9/1973 | Bitz ......................................... | 261/80 X |
| 5,240,478 | 8/1993 | Messina ................................. | 96/224 X |
| 5,399,319 | 3/1995 | Schoenberger et al. ................. | 96/224 |
| 5,523,057 | 6/1996 | Mazzilli ................................. | 96/224 X |
| 5,589,132 | 12/1996 | Zippel ..................................... | 96/224 X |

*Primary Examiner*—Richard L. Chiesa
*Attorney, Agent, or Firm*—Bereskin & Parr

[57] ABSTRACT

This invention relates to an air filtration system including four principle segments interconnected in series as one unit through which contaminated air is passed. The first segment includes a prefilter for the removal of dust particles; the second segment is provided with germicidal UV lamps for bacteria removal; the third segment contains a medicated wet filtration system for virus removal, and the fourth segment contains a final carbon filter.

6 Claims, 5 Drawing Sheets

AIR FILTRATION SYSTEM

BACKGROUND OF THE INVENTION

The invention relates generally to air filtration, but more specifically to a system which not only removes dust from an airflow, but particularly is designed to remove such particles and bacteria as are the principle causes of allergies.

Basic research in air filtration techniques discloses numerous systems for the removal of larger micron dust particles. In the main, these are small capacity units consisting in a fiber filter with a following carbon filter. These prior systems were in general ineffective, and incapable of handling large air flows, and were primarily designed for use and application in small enclosed spaces.

A basic need exists for a filtration system that can not only remove dust and odour, but can also provide a means of killing bacteria, germs, viruses, dust mites, spores and pollen which are regarded as major irritants to allergy sufferers.

A review of the prior art failed to uncover any system that could effectively meet this requirement.

SUMMARY OF THE INVENTION

Accordingly, it is an object of the present invention to provide a small, compact air filtration system that can not only handle large volumes of air, but can effectively remove contaminants such as referenced above.

The invention therefore provides a filtration system suitable for carrying out a method of air filtration including the steps of:

a) flowing air under pressure through a first filter of the type effective to remove large micron diameter particles;

b) flowing the air from said first filter through a second filter effective to remove particles of lesser micron diameter;

c) flowing the air from said second filter through a chamber containing ultraviolet germicidal lamps, effective to remove bacteria;

d) bringing the air from said chamber into contact with a germicidal vapor barrier effective to remove germs and any viruses remaining in the air flow; and e) flowing the air through a final carbon filter effective remove odours and particles left in the air flow.

The invention provides an air filtration system including a housing comprising of at least four inter-connected chambers through which air under pressure is caused to flow, the first of said chambers containing the first filter adapted for the removal of large micron particles of contaminants in said air flow; the second of said chambers containing ultraviolet germicidal lamps adapted to remove bacterial from said air flow; the third of said chambers containing a germicidal vapor barrier adapted to remove germs and viruses from said air flow; and the fourth chamber containing a carbon filter adapted for the removal of odour and any remaining particles of contaminant from said air flow.

BRIEF DESCRIPTION OF THE DRAWINGS

The invention will now be described by way of example only, reference being had to the accompany drawings, in which.

DESCRIPTION OF THE PREFERRED EMBODIMENTS

Figure 1:
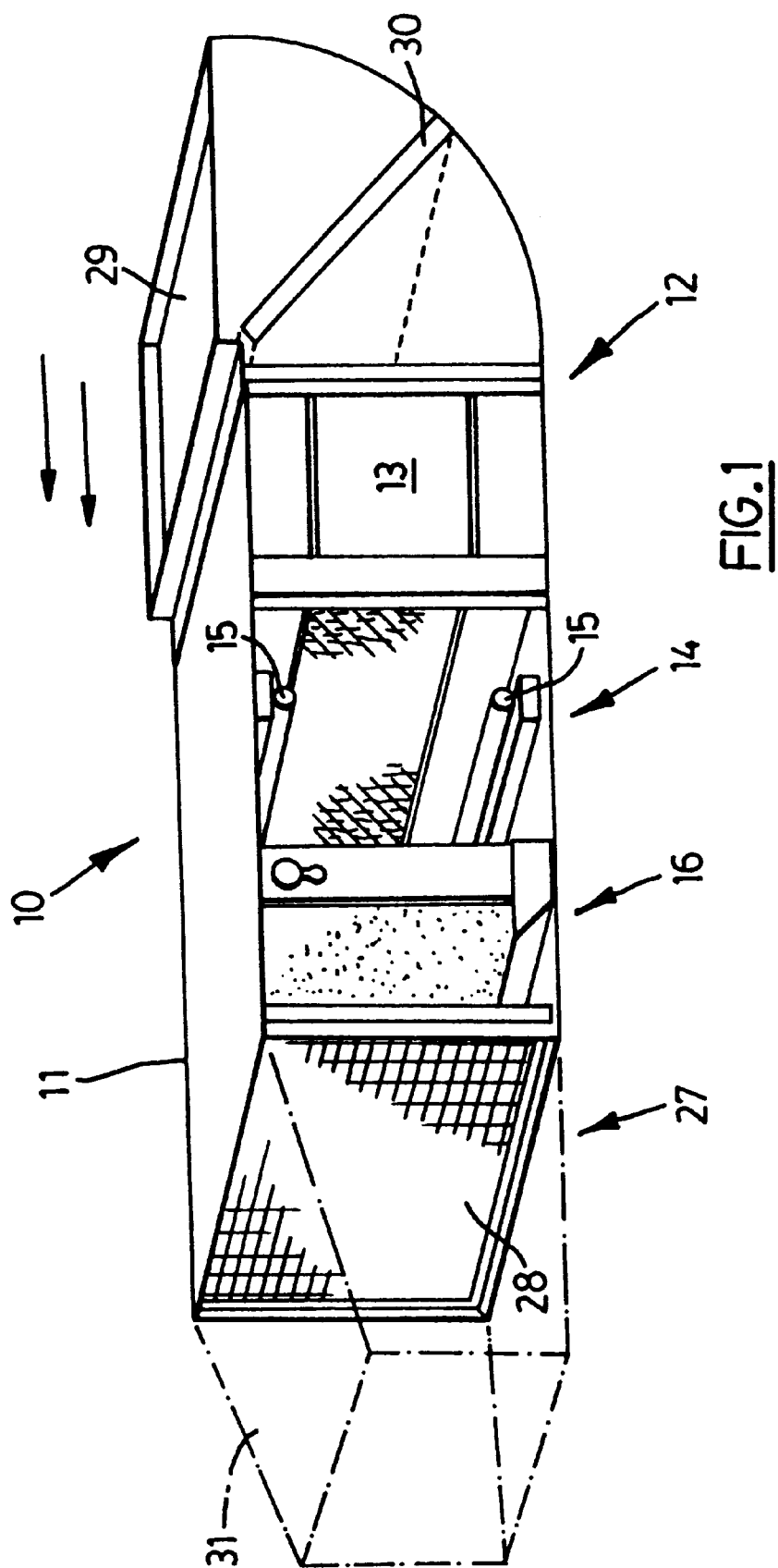
FIG. 1 is a schematic sectional view of the air filtration system of the present invention.

Looking firstly at the embodiment according to FIG. 1, the air filtration system 10 includes a housing 11 which comprises four basic sections interconnected longitudinally one with the other. The first section indicated at 12 contains a first high efficiency air filter 13 of the type generally referred to in the industry as a H.E.P.A. (Trademark) filter. This filter has a construction including waterproof glass as the filtration media and is effective in the removal down to 0.3 micron diameter particles.

The second section indicated at 14 contains an assembly consisting a pair of ultraviolet, germicidal lamps 15 which are low-pressure mercury vapor lamps transmitting short wave ultraviolet. This type of lamp is conventionally used in the treatment of bakery products and a variety of photochemical processes.

Figure 3:
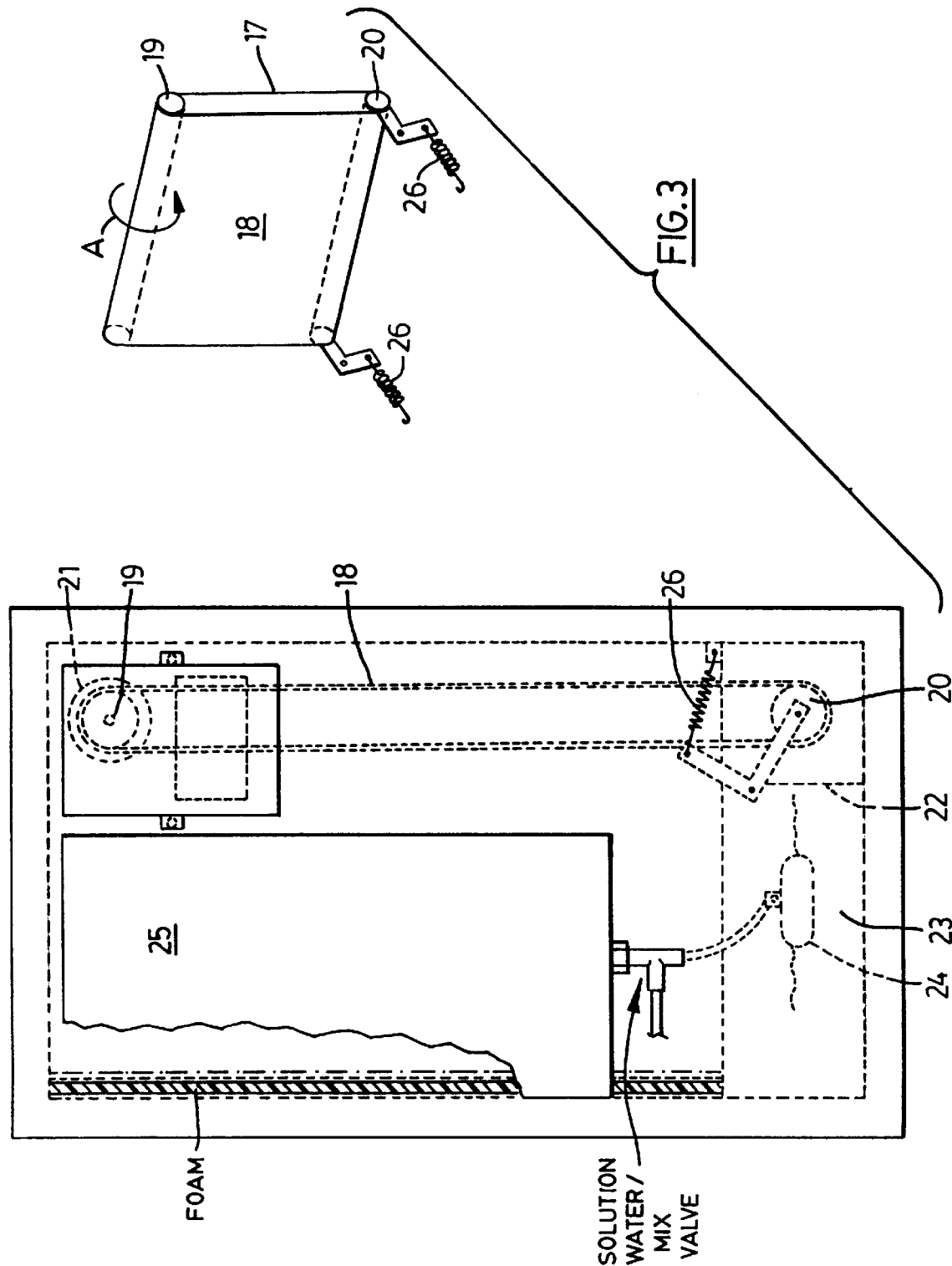
FIG. 3 is a side elevational view of the chamber containing the germicidal vapor barrier of this system according to FIGS. 1 and 2.
Figure 4:
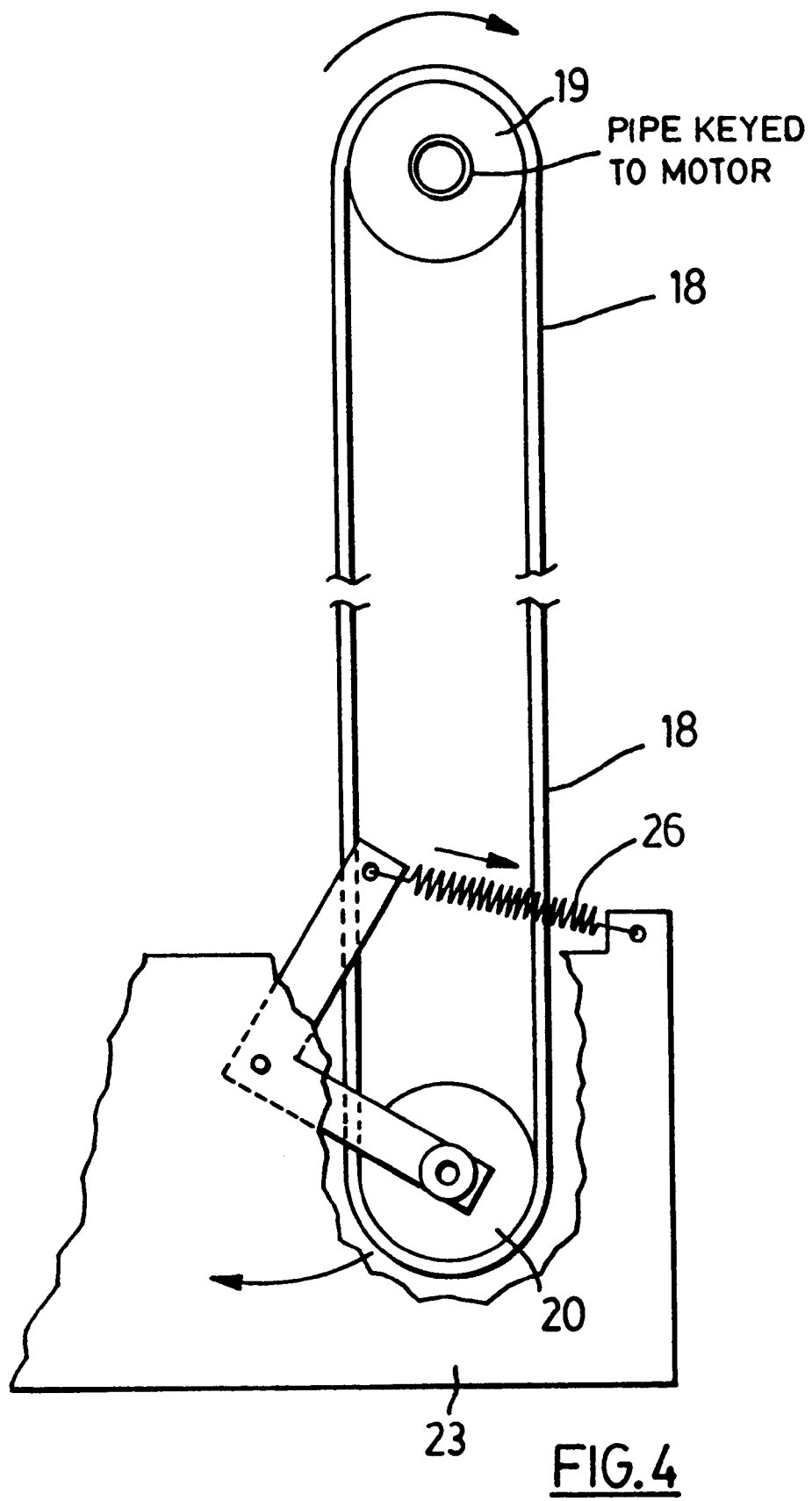
FIG. 4 is a detailed view of the vapor barrier assembly according to FIG. 3.

The third section indicated at 16 contains a vapor barrier assembly 17 (FIG. 3). This assembly includes a vertically arranged belt 18 of foam material, co-strained for movement in the direction of arrow A, around two rollers 19 and 20. Upper roller 19 being driven by a motor 21. A bath 22 is located in the area of roller 20, such that roller 20 and the foam belt passing around same is immersed in a germicidal solution 23. The assembly further includes a float system 24 to control the level of solution in the bath 22, the solution being supplied from a reservoir 25.

As can be seen from FIG. 3, rollers 19 and 20 are spring loaded at 26 to provide sufficient tension to the belt 18.

The fourth section generally indicated at 27 contains a conventional activated carbon filter 28. As additionally can be seen from FIG. 1, the inlet end 29 may also include a prefilter 30.

In operation, contaminated air is caused to flow under pressure through inlet 29 to initially pass through pre-filter 30, which is effective in removing large micron diameter particles. Air passing through pre-filter 30 is then caused to pass into section 12 and through H.E.P.A. filter 13, which as indicated above, is effective in the removal of small micron diameter particles.

From section 12 the air flow then passes through section 14 and is subjected in that section ultraviolet light emissions from lamp 15. Again, as indicated above, this ultraviolet emission is effective in the killing of bacteria.

From section 14 air then passes through the assembly to section 16 to come into contact with belt 18, which, as can be seen, is located such that it effectively blocks passage of air through the assembly thus ensuring contact of the air with the moving belt 18. Since the moving belt is being continually saturated with germicidal solution, any germs or virus in the air flow are effectively removed at this stage. Section 16 also provides for the replacement of humidity that may have been lost as a result of the air flow passing through section 14, which contains the ultraviolet lamps.

Finally, the air flow then enters section 27, which as mentioned above, contains a conventional activated carbon filter. This final filtration is necessary to remove odours and any particles of contaminant that may have been allowed to pass through the previous stages of the system.

As auxiliary fan unit indicated at 31 may be included in the system to assist in air flow.

Figure 2:
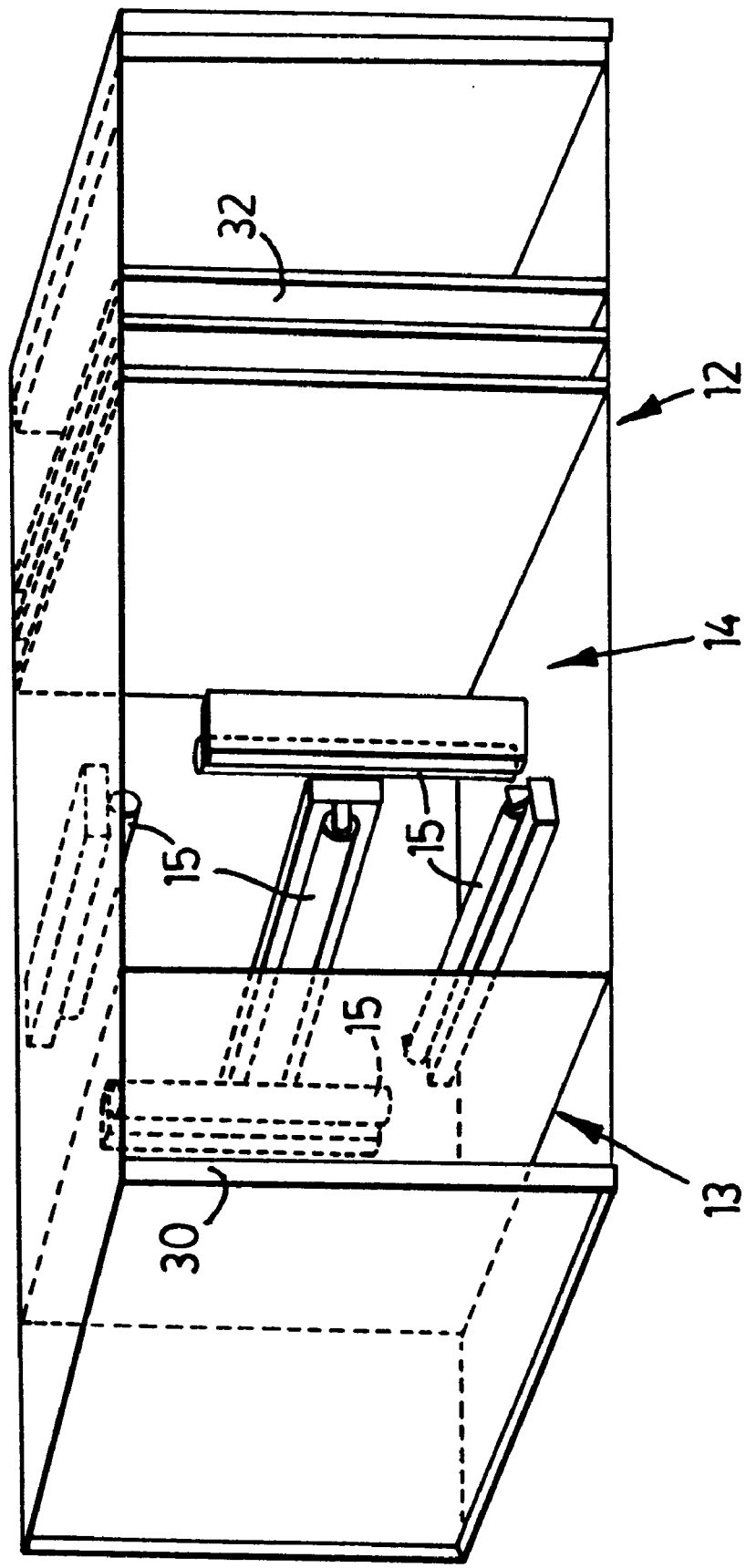
FIG. 2 is a schematic sectional view of a second embodiment of the air filtration system of the present invention.

Looking now to FIG. 2, a second embodiment of the invention is shown in the basic schematic form. The majority of the components previously described in relation to the embodiment of FIG. 1 are shown here, however, the system differs in that five ultraviolet lamps 15 are utilized in section 14, and the moving foam belt system of the first embodiment, located in section 12, has been replaced with a tri-panel foam/fiber sandwich 32. The germicidal solution being applied from a reservoir and sprayed via an injection system onto the face of the panel sandwich.

Figure 5:
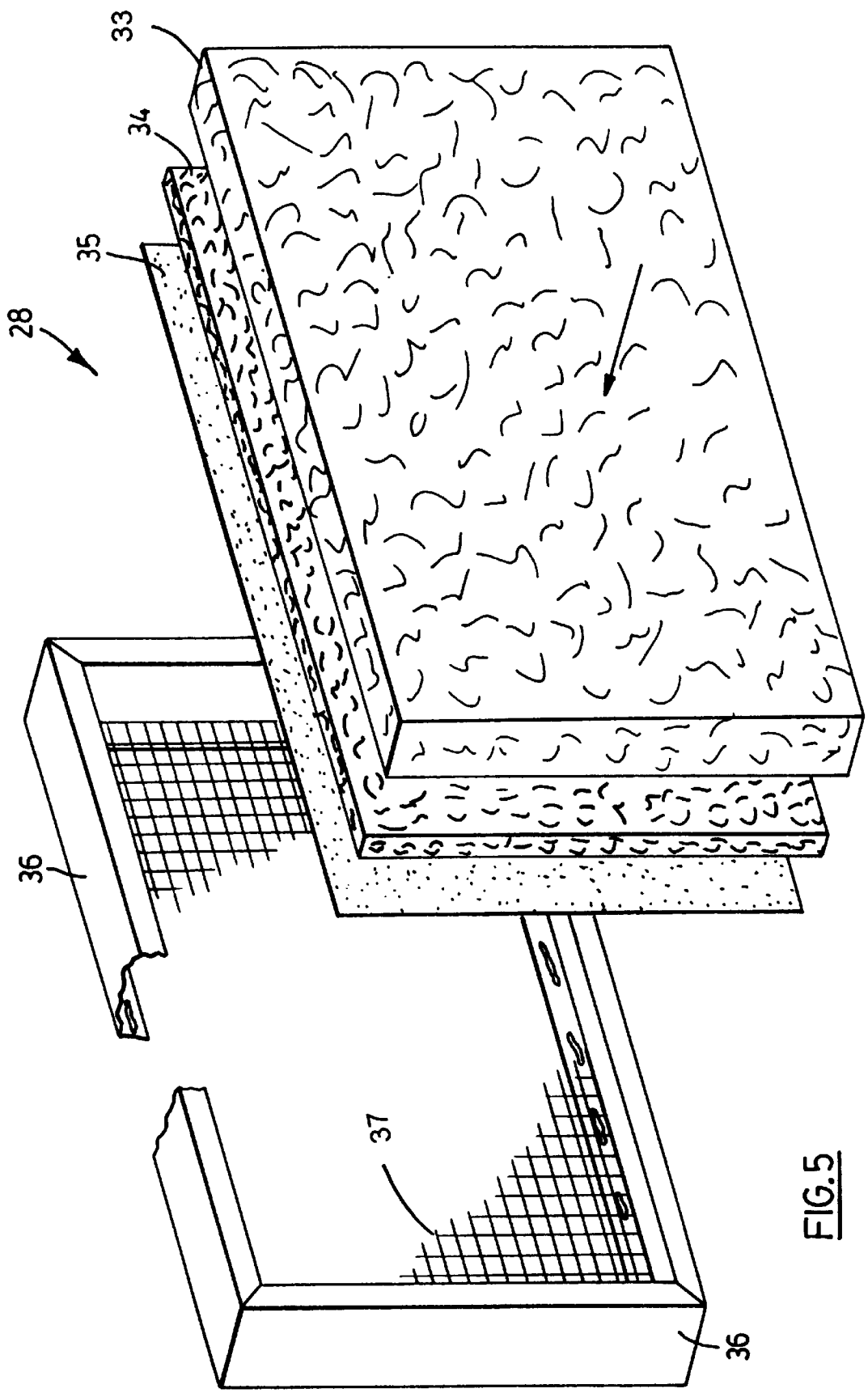
FIG. 5 is a perspective exploded view of an activated carbon filter in FIG. 1.

With reference to FIG. 5, the activated carbon filter 28 includes a number of layers, with the first layer being a layer of quilt batting 33. This is followed by a quarter-inch thick carbon filter sheet, comprising activated charcoal, indicated at 34. At the other side of the activated charcoal sheet 34, there is a single sheet 35, of 100% polyester non-woven interfacing. The sheets or layers 33, 34 and 35 are combined together and held in a frame 36 which is spot welded or soldered together. On the downstream side of the whole assembly, there is a one-quarter inch mesh bird screen 37.

The invention as described above is not intended to be limited by the structure disclosed. Various modifications and alternative arrangements of components can be included, however, it is important that any of the included arrangements, that are electrically activated, must precede any section in which vapour or moisture is present.

Reference is made, in relation to FIG. 3, and elsewhere to a vapor barrier 17. It will be understood that this element is a "barrier" only in the sense that it acts as a barrier, to prevent passage of certain living organisms. It is not a barrier, in the sense that it permits air to flow through it.

Accordingly, the invention shall be restricted only to the scope of the accompanying claims.

What I claim is:

1. A contaminated air filtration system including a housing comprising of at least four interconnected chambers through which air under pressure is caused to flow, the first of said chambers containing a first filter, comprising a H.E.P.A. filter adapted for the removal of particles of contaminants in said air flow down to at least 0.3 microns in size; the second of said chambers containing ultraviolet germicidal lamps adapted to remove bacteria from said airflow; the third of said chambers containing a germicidal vapour barrier adapted to remove germs and viruses from said air flow; and a fourth chamber containing a carbon filter adapted for the removal of odour and any remaining particles of contaminant from said air flow.

2. The system according to claim 1, wherein said first filter has its filtration media, waterproof glass.

3. The system according to claim 1 wherein said germicidal vapour barrier includes a conveyor belt, comprising a continuous belt of foam material constrained between two vertically positioned rollers, the upper of said rollers being driven, the lower of said rollers being immersed in a germicidal solution contained within bath means, such that upon rotation of said belt, solution is continuously fed to said belt to saturate same.

4. The system according to claim 3 wherein said rollers are maintained apart by spring means, to keep said belt in tension.

5. The system according to claim 3 wherein reservoir means is provided and a control means is connected to said reservoir means to control the level of solution in said bath.

6. A contaminated air filtration system comprising:

a housing defining at least four inter-connected cambers for air flow through the chambers sequentially;

a first filter within the first chamber, for removal of large micron particles of contaminants in said air flow down to at least 0.3 microns in size;

ultraviolet germicidal lamps mounted in the second chamber to remove bacteria from said air flow;

a germicidal vapour barrier mounted in the third chamber, for removal of germs and viruses from the air flow;

a carbon filter mounted in the fourth chamber for removal of odours and any remaining particles or contaminants from the air flow; and a fan means provided downstream from the fourth chamber for drawing air through the air filtration system.

* * * * *

UNITED STATES PATENT AND TRADEMARK OFFICE
CERTIFICATE OF CORRECTION

PATENT NO. : 6,063,170
DATED : July 25, 2000
INVENTOR(S) : Ronald H. Deibert

It is certified that error appears in the above-identified patent and that said Letters Patent is hereby corrected as shown below:

In column 1, line 50, delete "bacterial" and substitute --bacteria--.

In column 2, line 21, after "treatment" insert -- of air, for the disinfection of water, the surface treatment--.

In column 2, line 25, delete "co-strained" and substitute --constrained--.

In column 3, line 9, delete "applied" and substitute --supplied--.

In claim 2, line 2, after "filter has" insert --as--.

In claim 6, line 2, delete "cambers" and substitute --chambers--.

Signed and Sealed this

Seventeenth Day of April, 2001

Attest:

NICHOLAS P. GODICI

Attesting Officer    Acting Director of the United States Patent and Trademark Office